(12) United States Patent
Alshehri et al.

(10) Patent No.: US 9,446,230 B1
(45) Date of Patent: Sep. 20, 2016

(54) COCHLEAR IMPLANT ELECTRODE ARRAY AND METHOD FOR INSERTING THE SAME INTO A HUMAN COCHLEA

(71) Applicant: Advanced Bionics AG, Staefa (CH)

(72) Inventors: Hassan Alshehri, Riyadh (SA);
Abdulrahman Hagr, Riyadh (SA);
Patrick Joseph Boyle, Kent (GB);
Volkmar Hamacher, Hannover (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/477,795

(22) Filed: Sep. 4, 2014

(51) Int. Cl.
*A61N 1/05* (2006.01)

(52) U.S. Cl.
CPC .................................. *A61N 1/0541* (2013.01)

(58) Field of Classification Search
CPC . A61N 1/0541; A61N 1/36032; A61N 1/372
USPC .............................................. 607/55–57, 137
See application file for complete search history.

(56) References Cited

U.S. PATENT DOCUMENTS

| | | | |
|---|---|---|---|
| 4,148,307 A | 4/1979 | Utsugi | |
| 5,578,084 A | 11/1996 | Kuzma et al. | |
| 5,824,031 A * | 10/1998 | Cookston | A61M 25/01 607/122 |
| 6,074,422 A * | 6/2000 | Berrang | A61N 1/0541 607/137 |
| 6,266,568 B1 * | 7/2001 | Mann | A61N 1/0541 607/137 |
| 6,408,855 B1 | 6/2002 | Berrang et al. | |
| 7,194,314 B1 * | 3/2007 | Richter | A61N 1/36032 600/25 |
| 7,319,906 B2 | 1/2008 | Kuzma et al. | |
| 7,822,482 B2 | 10/2010 | Gerber | |
| 8,229,574 B2 | 7/2012 | Parker et al. | |
| 2002/0029055 A1 * | 3/2002 | Bonutti | A61B 10/025 606/170 |
| 2004/0127968 A1 * | 7/2004 | Kuzma | A61N 1/0541 607/137 |
| 2004/0176757 A1 * | 9/2004 | Sinelnikov | A61B 17/22004 606/27 |
| 2006/0106442 A1 | 5/2006 | Richardson et al. | |
| 2007/0299303 A1 | 12/2007 | Ogikubo | |
| 2010/0249505 A1 | 9/2010 | Shoham et al. | |
| 2011/0106101 A1 * | 5/2011 | Tortonese | A61N 1/0541 606/129 |
| 2013/0238067 A1 | 9/2013 | Baudino | |
| 2015/0367101 A1 | 12/2015 | Shoham et al. | |

FOREIGN PATENT DOCUMENTS

| | | |
|---|---|---|
| AU | 199711701 | 8/1997 |
| EP | 2114260 | 4/2013 |
| WO | WO-2005/123707 | 12/2005 |
| WO | WO-2012/154179 | 11/2012 |

\* cited by examiner

*Primary Examiner* — Eugene Wu
(74) *Attorney, Agent, or Firm* — ALG Intellectual Property, LLC (57) ABSTRACT

An exemplary cochlear electrode array includes a flexible body having a pre-curved spiral shape so as to conform with the curvature of a human cochlea, a plurality of stimulation electrode contacts spaced apart along a first side of the flexible body, a bundle of wires embedded within the flexible body for electrically connecting the electrode contacts to at least one stimulation signal source, at least one inflatable portion extending along at least part of the length of the flexible body, the at least one inflatable portion being adapted to straighten the flexible body, starting from the pre-curved shape, prior to insertion into the cochlea upon being inflated by being filled with gas or liquid, and to allow the flexible body to gradually reassume its pre-curved shape during insertion of the flexible body into the cochlea upon gradual withdrawal of gas or liquid from the at least one inflatable portion.

12 Claims, 9 Drawing Sheets

COCHLEAR IMPLANT ELECTRODE ARRAY AND METHOD FOR INSERTING THE SAME INTO A HUMAN COCHLEA

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how intense the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Current designs of cochlear implant electrode arrays distribute their electrode contacts to various intra-cochlear positions. There is variability in the medial-lateral position, rotational orientation with respect to the modiolus and distribution along the length of the scala tympani. Attempts to control medial-lateral position use preformed designs that aim for a medial position but have no control over length, or rotational orientation in a helical-spiral space. Mid-scala arrays largely control for rotational insertion depth but lead to variability in the medial-lateral direction and also suffer from rotational variability. There are some attempts at accounting for cochlear size through offering a range of array lengths. However, these are only offered for straight arrays that leave the contacts in a lateral position. A design that used a wedge shaped positioner to accommodate a range of cochleae was withdrawn due to safety issues.

A cochlear implant electrode array must distribute its contacts so that discrete bundles of VIIIth nerve fibers are addressed by each contact, hence creating independent channels of information. This is best done by placing the contacts as close to the neural population as possible, meaning adjacent to the medial wall of the cochlea, immediately behind which the target spiral ganglion cells are located. However, the cochlea is buried in the hardest bone of the body, and so offers very limited access.

Also, there is a considerable variation in the size of individual cochleae and in their shape. Usually human cochleae have around 2.5 turns and take a spiral-helical form. To minimize damage to the highly delicate cochlear structures, electrode arrays tend to be introduced via one of the existing openings of the cochlea, the round window, or via a surgically extended round window. This limits the size of the array to under 1 mm diameter. Moreover, the scala tymapani varies in its lateral dimension from under 0.5 mm to over 3 mm along its length, compounded by variation in all other aspects of the cochlea U.S. Pat. No. 6,266,568 B1 relates to a cochlear electrode array comprising a flexible body on which electrode contacts are carried along a medial side; the flexible body includes an inflatable compartment at the distal end of the electrode array on a side of the flexible body that is opposite the electrode contacts. The electrode array is inserted into the cochlea to a desired depth while the inflatable compartment remains in a deflated state, whereafter a desired modiolus-hugging position is achieved by inflating the inflatable compartment by injecting therein a bio-compatible fluid.

U.S. Pat. No. 7,194,314 B1 relates to an implantable cochlear electrode array comprising a membrane which may be inflated to anchor the array in a position in the cochlea with the electrode contacts pressed into contact with the modular wall, allowing the membrane to seal with the surrounding tissue of the cochlea; the inflatable membrane is inflated once the electrode array has reached its final position.

U.S. Pat. No. 7,822,482 B1 relates to an implantable electrical lead including a rounded array of electrodes which is partly inflatable in order to get closer to a target stimulation site.

U.S. Pat. No. 5,578,084 relates to a cochlear implant electrode array comprising a layer having a controlled rate of expansion when exposed to the water contained in body fluids, making the layer to expand in use and curving the implanted electrode array in order to enable more effective stimulation.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 1B and 1C are views of the positioning of an electrode array of the system of FIG. 1A within the cochlea.

DETAILED DESCRIPTION

In some examples, a cochlear electrode array is provided that allows for accurate placement of the electrode contacts at a desired location in the individual cochlea of the patient. A system and method are also provided for inserting such cochlear electrode array into the patient's cochlea.

The systems and methods described herein are beneficial in that, by straightening a pre-curved flexible body of the cochlear electrode array by inflating at least one inflatable portion extending along at least part of the length of the flexible body prior to insertion into the cochlea and by allowing the flexible body to gradually reassume its pre-curved shape during insertion of the flexible body into the cochlea upon gradual withdrawal of gas or liquid from the at least one inflatable portion, an insertion process can be realized which can be adapted to the individual geometry of the patient's cochlea, thereby enabling particularly accurate positioning of the electrode array, while reducing the cochlea's susceptibility to trauma upon insertion of the electrode array.

These and further features and advantages of the present systems and methods will become apparent from the following description when taken in connection with the accompanying drawings.

Figure 1A:
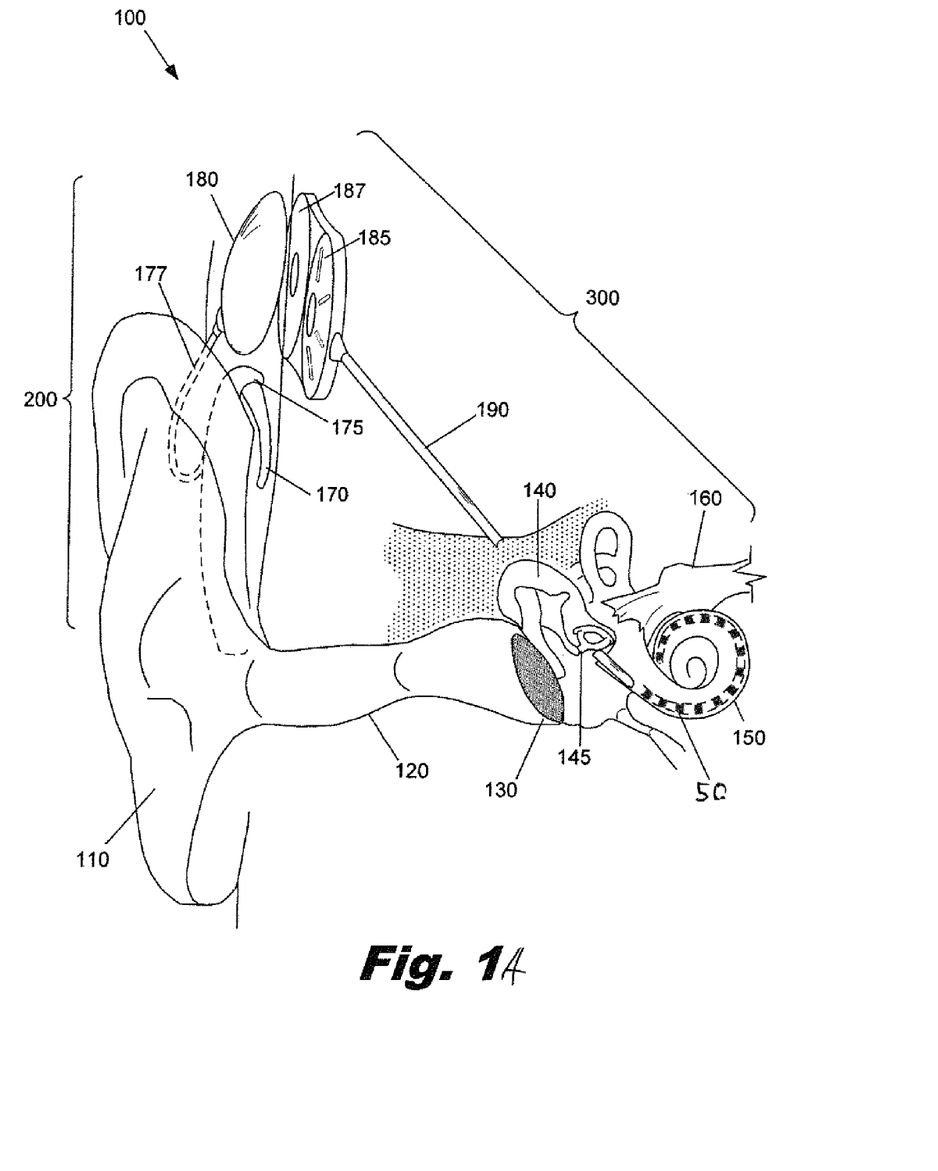
FIG. 1A is an illustrative diagram showing an example of a cochlear implant system in use.

FIG. 1A is a diagram showing an illustrative cochlear implant system 100 having a cochlear implant 300 with an electrode array 50 that is surgically placed within the patient's cochlea 150. Ordinarily, sound enters the external ear, or pinna, 110 and is directed into the auditory canal 120 where the sound wave vibrates the tympanic membrane 130. The motion of the tympanic membrane 130 is transmitted through the ossicular chain 140, which includes of three bones in the middle ear. The third bone of the ossicular chain 140, the stapes 145, contacts the outer surface of the cochlea 150 and causes movement of the fluid within the cochlea 150. Cochlear hair cells respond to the fluid-borne vibration in the cochlea 150 and trigger neural electrical signals that are conducted from the cochlea to the auditory cortex by the auditory nerve 160.

As indicated above, the cochlear implant 300, is a surgically implanted electronic device that provides a sense of sound to a person who is profoundly deaf or severely hard of hearing. The cochlear implant system 200, 300 operates by direct electrical stimulation of the auditory nerve cells, bypassing the defective cochlear hair cells that normally transduce acoustic energy into electrical energy.

External components 200 of the cochlear implant system can include a Behind-The-Ear (BTE) unit 175, which contains the sound processor and has a microphone 170, a cable 177, and a transmitter 180. The microphone 170 picks up sound from the environment and converts it into an electrical signal. The sound processor within the BTE unit 175 first converts the microphone signal into a digital signal, then selectively filters and manipulates the this signal, finally sending processed electrical signals through the cable 177 to the transmitter 180. The transmitter 180 receives the processed electrical signals from the processor and transmits them to the implanted antenna 187 by electromagnetic transmission.

The components of the cochlear implant 300 include an internal processor 185, an antenna 187, and a cochlear lead 190 having an electrode array 50. The internal processor 185 and antenna 187 are secured beneath the user's skin, typically above and behind the pinna 110. The antenna 187 receives signals and power from the transmitter 180. The internal processor 185 receives these signals and performs one or more operations on the signals to generate modified signals. These modified signals are then sent along a number of signal wires that pass through the cochlear lead 190 and are individually connected to the electrodes in the electrode array 50. The electrode array 50 is implanted within the cochlea 150 and provides electrical stimulation to the auditory nerve 160.

The cochlear implant 300 stimulates different portions of the cochlea 150 according to the frequencies detected by the microphone 170, just as a normal functioning ear would experience stimulation at different portions of the cochlea depending on the frequency of sound vibrating the liquid within the cochlea 150. This allows the brain to interpret the frequency of the sound as if the hair cells stimulated by the basilar membrane were functioning properly.

Figure 2A:
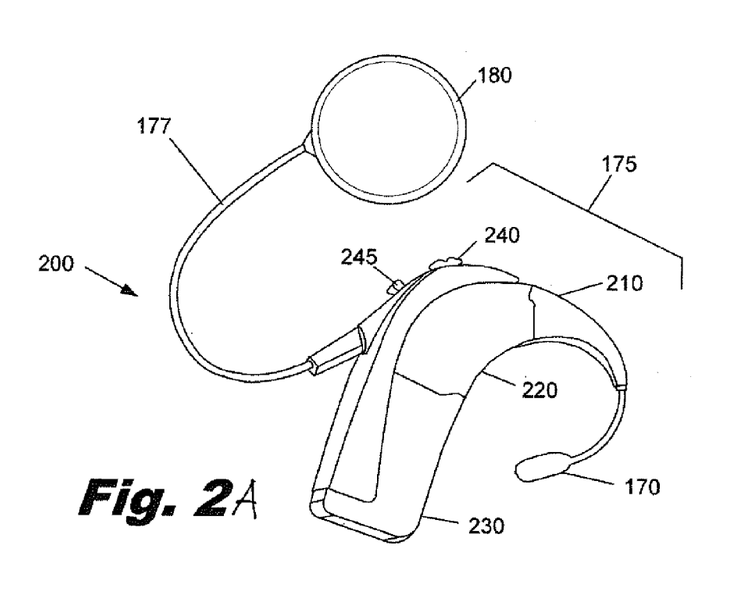
FIGS. 2A and 2B are diagrams showing respectively the external and internal components of the cochlear implant system of FIG. 1A.

FIG. 2A is an illustrative diagram showing a more detailed view of the external components 200 of a cochlear implant system. External components 200 of the cochlear implant system include a BTE unit 175, which comprises a microphone 170, an ear hook 210, a sound processor 220, and a battery 230, which may be rechargeable. As already mentioned above, the microphone 170 picks up sound from the environment and converts it into electrical impulses, and the sound processor 220 selectively filters and manipulates the electrical microphone signal and sends the processed electrical signals through a cable 177 to the transmitter 180. A number of controls 240, 245 adjust the operation of the processor 220. These controls may include a volume switch 240 and program selection switch 245. The transmitter 180 receives the processed electrical signals from the processor 220 and transmits these electrical signals and power from the battery 230 to the cochlear implant 300 by electromagnetic transmission.

Figure 1B:
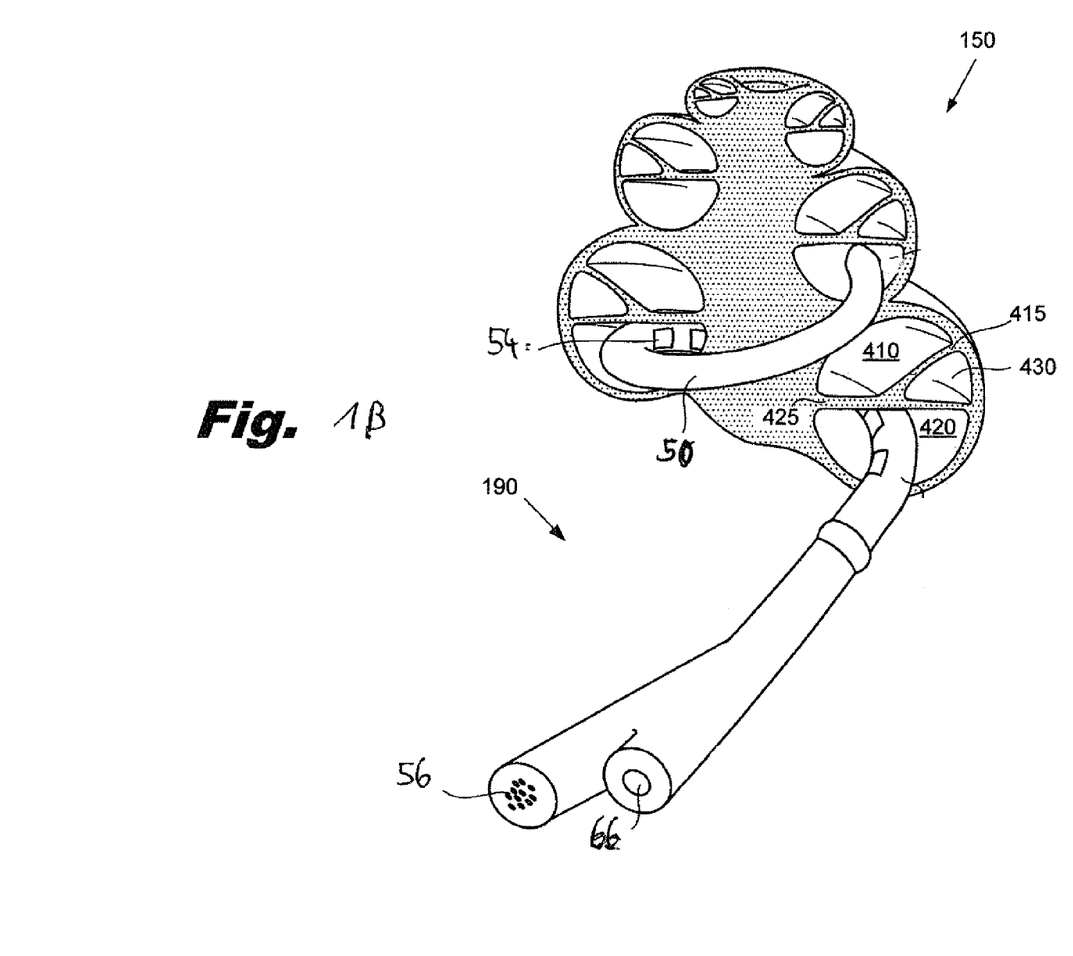
Figure 2B:
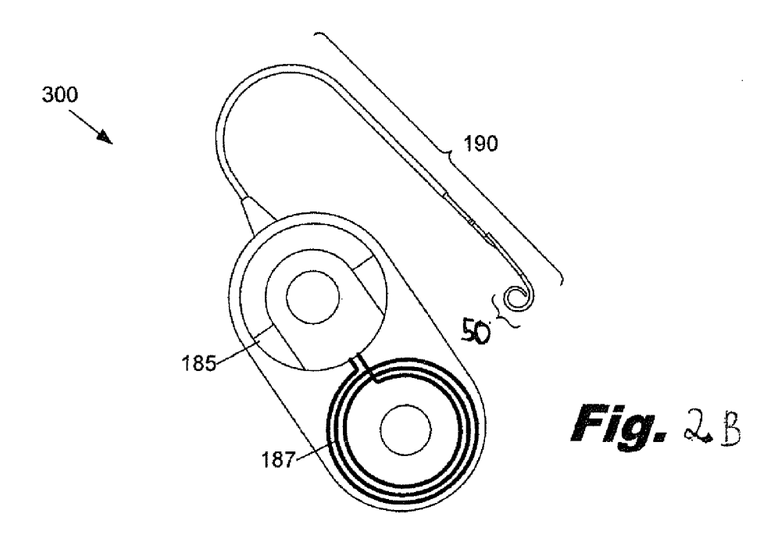

FIG. 2B is an illustrative diagram showing an example of a cochlear implant 300, including an internal processor 185, an antenna 187, and a cochlear lead 190 having an electrode array 50. The cochlear implant 300 is surgically implanted such that the electrode array 50 is internal to the cochlea, as shown in FIG. 1B. The internal processor 185 and antenna 187 are secured beneath the user's skin, typically above and behind the pinna 110, with the cochlear lead 190 connecting the internal processor 185 to the electrode array 50 within the cochlea. As discussed above, the antenna 187 receives signals from the transmitter 180 and sends the signals to the internal processor 185. The internal processor 185 modifies the signals and passes them along the appropriate wires to activate one or more of the electrodes within the electrode array 50. This provides the user with sensory input that is a representation of external sound waves sensed by the microphone (170).

The cochlear lead 190 may be formed using a two-step molding process. In this example (FIG. 3C), the cochlear lead 190 includes an electrode array 50 made up of electrodes 54, a wire bundle 56 that electrically connects each of the electrodes/electrode contacts 54 to the internal processor 185 (FIG. 2B), and a flexible body 52 that encapsulates the wires 56 and electrodes 54. As discussed above, the cochlea has a spiral shape. The electrode array 50 may have a tight curvature that matches the interior geometry of the cochlea. For example, the apical portion of the electrode array 50 may have a radius of curvature R between 1.5 and 1.8 millimeters. The radius of curvature in the electrode array 50 is formed by placing the wires 56 and electrodes 54 in a mold and then filling the mold with a curable encapsulant. For example, the curable encapsulant may be medical grade silicone. The mold has a tighter radius of curvature than the cochlea. When the electrode array 50 is removed from the mold, the electrode array 50 opens up slightly to a relaxed state. The relaxed state balances the forces produced by the wires and the flexible body. In general, the straight wires tend to open up the electrode array and the silicone tends to resist this opening motion. In the relaxed state, these forces are balanced and the shape of the electrode array approximates the geometry of the interior of the cochlea.

An illustrative two-step molding apparatus and process are described in U.S. Pat. No. 7,319,906 by Janusz Kuzma et al., which patent is incorporated herein by reference in its entirety.

FIG. 1B is a cross sectional view of a cochlea 150 and shows an illustrative electrode array 50 placed within the cochlea 150. As discussed above, the primary structure of the cochlea 150 is a, helically coiled, hollow in the temporal bone, similar to a nautilus shell. The coiled tube is divided through most of its length into three fluid-filled spaces (scalae). The scala vestibuli 410 is partitioned from the scala media 430 by Reissner's membrane 415 and lies superior to it. The scala tympani 420 is partitioned from the scala media 430 by the basilar membrane (in FIG. 1B the the osseous spiral lamina (OSL) is shown at 425, with the basilar membrane being the section lateral to the OSL, in FIG. 1B towards the top of the figure, above where Reissner's membrane joins) and lies inferior to it. A typical human cochlea includes approximately two and a half helical turns of its various constituent channels. The electrode array 50 is inserted into one of the scalae, typically the scala tympani 420, to bring the individual electrodes into close proximity with the tonotopically organized nerves.

FIG. 1C shows a cross sectional view of a single coil of the cochlea 150. As discussed above, the coiled tube is divided into three fluid-filled spaces 410, 420, 430. The scala vestibuli 410 is partitioned from the scala media 430 by Reissner's membrane 415 and lies superior to it. The scala tympani 420 is partitioned from the scala media 430 by the basilar membrane and lies inferior to it. The bony walls of the cochlea are lined with a membrane, called the endosteum 460, which, between the scala media and scala tympani, is greatly thickened and called the spiral ligament 456. The spiral ligament 456 connects the basilar membrane 425 to the wall of the cochlea.

The cochlea 150 is filled with fluid that moves in response to the vibrations coming from the middle ear via the stapes 145, FIG. 1A). As the fluid moves, a tectorial membrane 453 and thousands of hair cells 451 in a normal, functioning cochlea are set in motion. The hair cells 451 convert that motion to electrical signals that are communicated via neurotransmitters to the auditory nerve 160, and transformed into electrical impulses known as action potentials, which are propagated to structures in the brainstem for further processing (in FIG. 1C 451 indicates the three rows of outer hair cells; the single row of inner hair cells below this actually do the transduction, with the outer hair cells producing amplification of basilar membrane movement, increasing the sensitivity of the transduction process). The electrode array is inserted into the scala tympani 420 and the electrical potentials generated by the electrodes stimulate the auditory nerve 160.

The electrode array may be positioned within the scala tympani 420 in one of three general positions that are shown as dashed circles. A medial position 495 locates the electrode array in proximity to the medial wall. A lateral position 497 locates the electrode array in proximity to the lateral wall and adjacent to the spiral ligament 456. Insertion in either of these two positions can involve frictional contact between the electrode array and the walls of the cochlea. This frictional contact may increase the forces used to insert the electrode array into the cochlea.

A third position is the mid-scalar position 496 that locates the electrode array near the center of the scala tympani 420. This position minimizes contact and frictional forces between the electrode array and the walls of the scala tympani. However, achieving an electrode geometry that has both a small cross section and the desired shape for mid-scalar placement can be challenging.

Figures 3A, 3B:
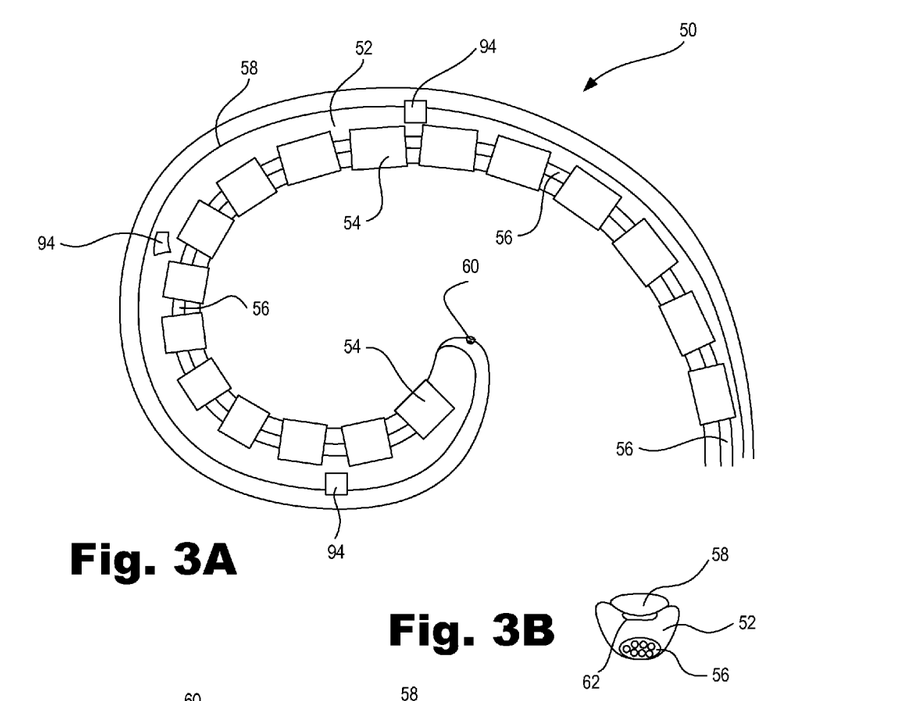
FIGS. 3A and 3B are a schematic side view and a cross-sectional view, respectively, of an example of an electrode array in a deflated state.
Figure 3C:
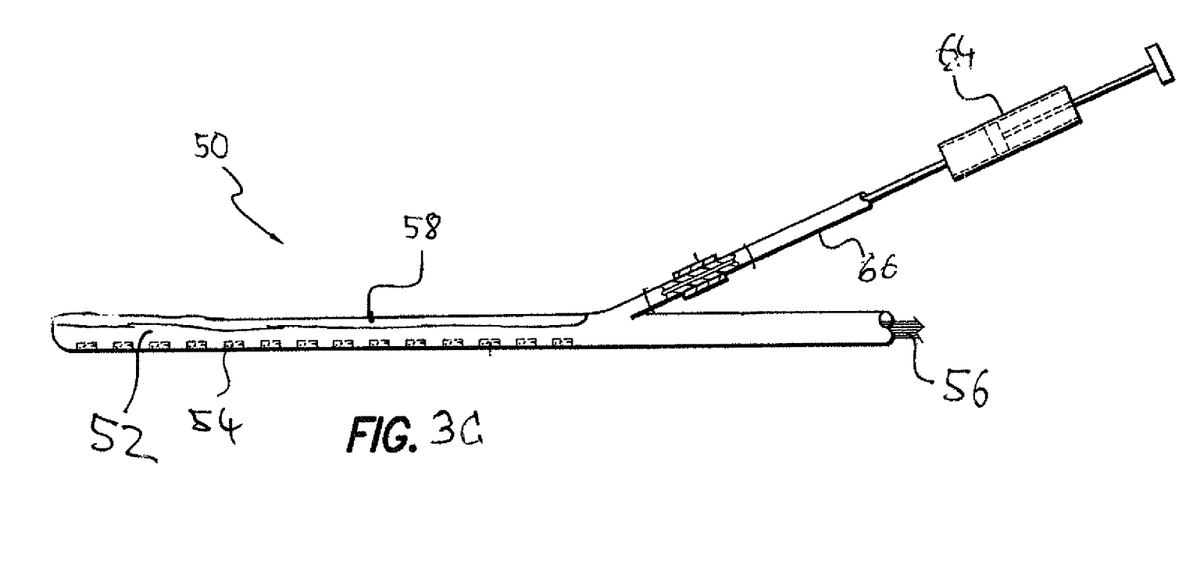
FIG. 3C is a side view of an example of the electrode array of FIGS. 3A and 3B when being inflated.

FIG. 3A is a schematic side view of a distal (apical) portion of an example of an electrode array 50 comprising a flexible body 52 having a plurality of stimulation electrode contacts 54 disposed on one side, namely the side facing the modiolus when the electrode array 50 is placed in the cochlea 150. The contacts 54 are connected to the processor 185 via wires 56. As already mentioned above, the flexible body 52, which may be made of, for example, silicone, is provided with a pre-curved shape so as to conform with the curvature of a human cochlea in order to follow, for example, the geometry of the scala tympani; such shape has a substantially spiral/helical geometry. The pre-curved shape may be obtained by one of the methods known in the art, such as by appropriate molding of the body 52, by inserting a mechanical rib in the body 52 or by providing the wire bundle 56 with an appropriate curvature; to this end, also shape memory materials may be used.

In addition, the electrode array 50 comprises an inflatable balloon 58 extending along at least part of the length of the flexible body 52 at the side of the flexible body 52 opposite to the side carrying the electrode contacts 54, i.e. at the side facing away from the modiolus when the electrode array 50 is inserted into the cochlea 150. The balloon 58 is attached to the flexible body 52 at at least two attachment points 60. The balloon 58 preferably is arranged at least in part within an axially extending depression (or trough) 62 of the flexible body 52 (see the cross-sectional view shown in FIG. 3B). Typically, one of the attachment points 60 is provided at one end of the balloon 58, and the other one of the attachment points 60 is provided at the other end of the balloon 58. Usually the balloon 58 is connected to the flexible body 52 at the attachment point 60 only, i.e. in between the attachment points 60 there is no connection between the balloon 58 and the flexible body 52.

In FIGS. 3A and 3B a deflated state of the balloon 58 is shown, in which the flexible body 52 assumes its pre-curved shape.

The balloon 58 may be inflated by filling the balloon 58 with a gas or a liquid, which may be supplied by, for example, a syringe 64 via a supply channel 66 (see FIG. 3C) in order to straighten the flexible body 52 against its pre-curvature of FIG. 3A in order to act as an "air stylet", providing for a straightened electrode array 50 prior to insertion into the cochlea. In such inflated state, as shown in FIGS. 4A and 4B, the inflated balloon 58 may have a tubular shape with a substantially circular cross-section, i.e. the inflated balloon 58 may have a substantially cylindrical shape.

When the electrode array 50 is being inserted into the cochlea 150 (typically into the scala tympani), the balloon 58 is gradually deflated by gradual withdrawal of at least some of the gas/liquid filling the balloon 58, thereby allowing the flexible body 52 to gradually reassume its pre-curved shape in the course of the insertion of the flexible body into the cochlea. By providing for such gradual release of the pre-curved spiral/helical shape of the flexible body 52 according to the progress of the insertion procedure, the forces acting on the cochlea, and thus potential trauma to the cochlea, can be reduced. In particular, the present curvature of the flexible body 52 can be adapted, during insertion into the cochlea, to the individual shape of the cochlea. Control of the withdrawal of liquid/gas from the balloon 58 during insertion may be achieved by correspondingly operating the syringe 64.

Figures 4A, 4B:
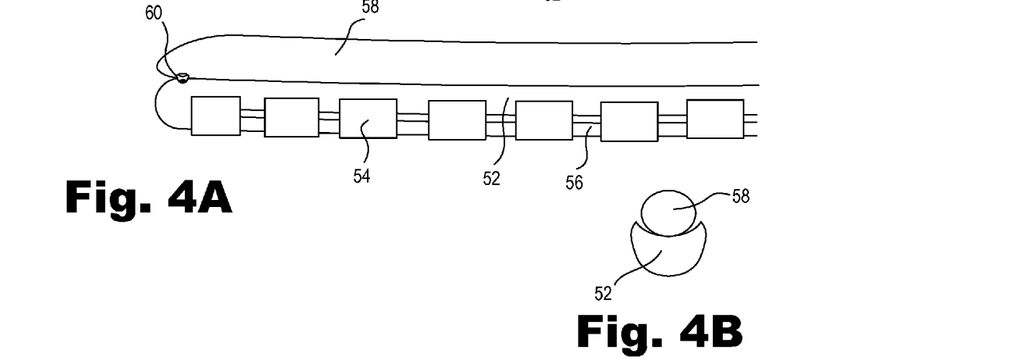
FIGS. 4A and 4B are views like FIGS. 3A and 3B, respectively, with the electrode array being shown in an inflated state.
Figure 4C:
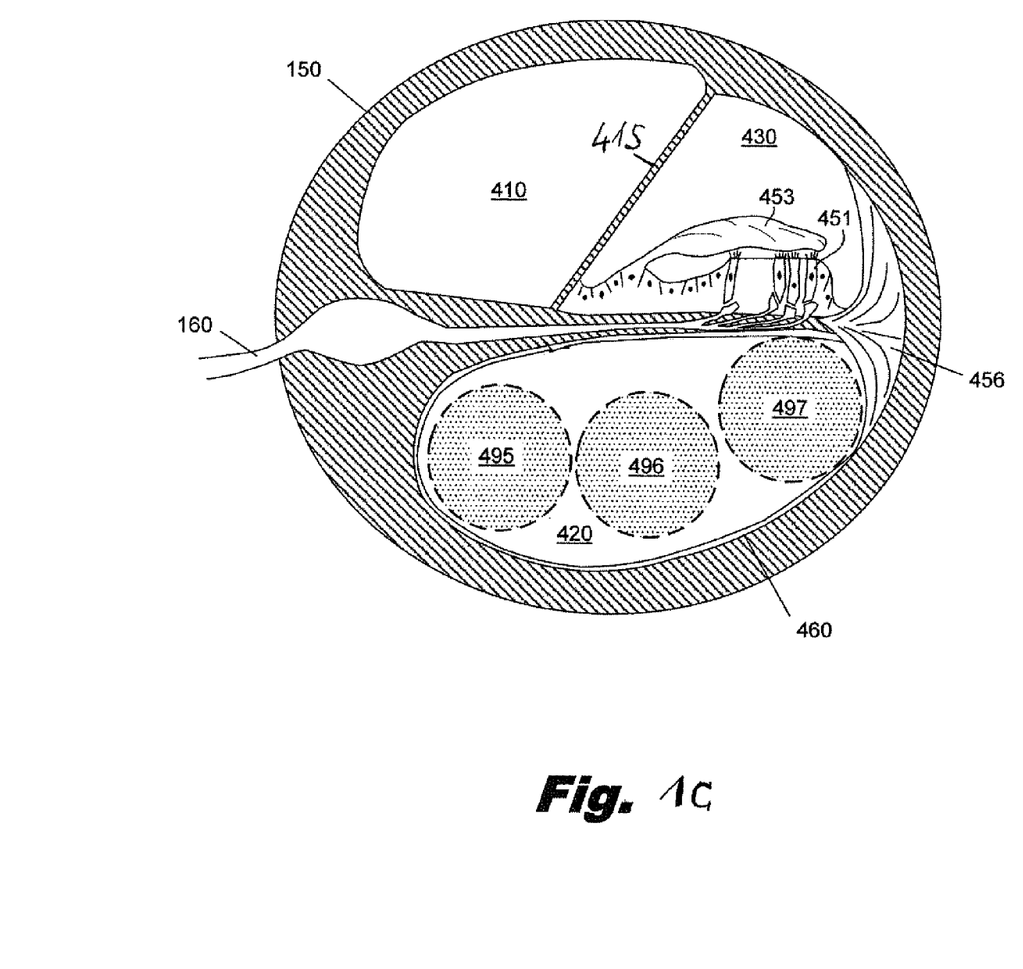
Figure 5A:
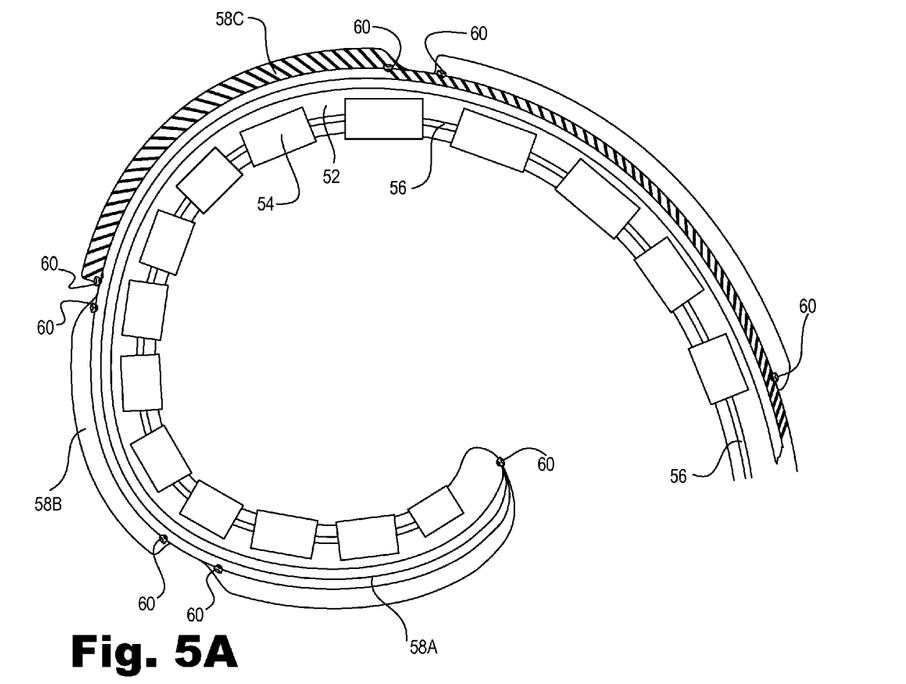
FIGS. 5A and 5B are views like FIGS. 3A and 3B, respectively, wherein an alternative example of the electrode array is shown.
Figure 5B:
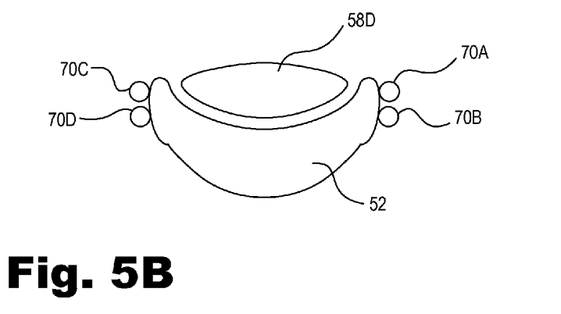

According to an alternative embodiment shown in FIGS. 5A and 5B, the single balloon 58 of the embodiment shown in FIGS. 3 and 4 is replaced by a plurality of balloons 58A, 58B, 58C and 58D which are inflatable/deflatable separately from each other and which are arranged in series along at least part of the length of the flexible body 52. Each of the balloons 58A to 58D is attached to the flexible body 52 via at least two attachment points 60 at each of the ends of the respective balloon. Each balloon 58A to 58D is connected to a dedicated gas/liquid supply tube 70A to 70D, respectively, which may laterally extend along the surface of the flexible body 52, see in particular FIG. 5B. By providing such plurality of individually inflatable/deflatable balloons 58A-58D, finer control of the release of the straightened shape to the pre-curved shape during insertion into the cochlea can be achieved.

Figure 6:
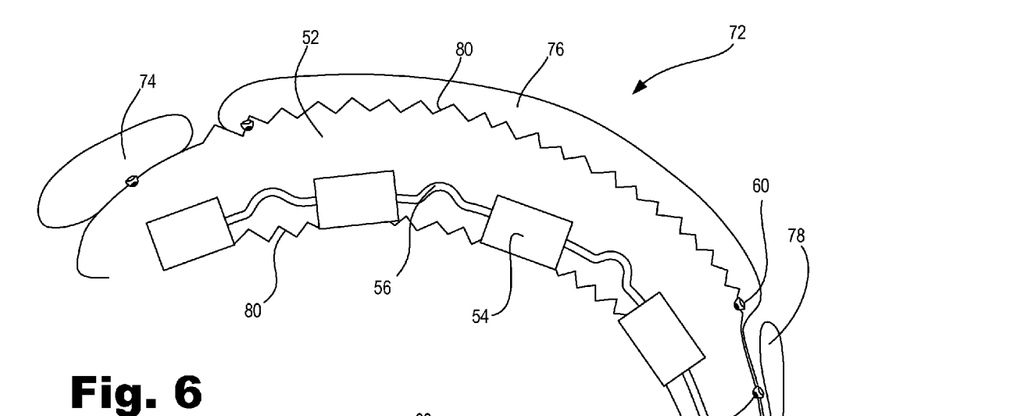
FIG. 6 is a schematic side view of the tip portion of a further example of an electrode array in a deflated state.

In FIG. 6 an alternative embodiment is shown, wherein the distal (apical) portion of the electrode array 50 is provided with a balloon arrangement 72 comprising a first locking balloon 74 located at or close to the tip of the flexible body 52, a stretching balloon 76 and a second locking balloon 78, with the stretching balloon 76 being located axially between the first locking balloon 74 and the second locking balloon 78. The balloons 74, 76, 78 are attached to the side of the flexible body 52 facing away from the modiolus when the electrode array 50 is inserted in the cochlea; for the locking balloons 74, 78 one attachment point 60 may be sufficient, whereas the stretching balloon 76 is provided with an attachment point at each of its ends. The portion of the flexible body 52 located at the stretching balloon 76 is axially flexible in such a manner that it may be axially stretched upon inflation of the stretching balloon 76. To this end, that portion of the flexible body 52 may be provided with wrinkled walls 80, i.e. it may be provided with a zig-zag wall structure. Further, the wire bundle 56 connecting to the electrode contacts 54 preferably is provided with a flexural geometry, as described, for example, in WO 2012/154179 A1, so that the axial distance between the contacts 54 may increase in order to allow the stretching balloon 76 to axially stretch the portion of the flexible body 52 adjacent to the stretching balloon 76.

Each of the balloons 74, 76, 78 is separately inflatable/deflatable in such a manner that the balloon assembly 72 may be used for "marching" the electrode array 50 into or out of the cochlea. Such "marching" motion may be achieved by the following inflation/deflation sequence:

In a first step, the first and second locking balloons 74, 78 are inflated, thereby blocking movement of the flexible body 52 within the cochlea by engagement with the cochlea wall at a position of the first locking balloon 74 and the second locking balloon 78, respectively. In a second step, the stretching balloon 76 is inflated, while the first locking balloon 74 is deflated, thereby releasing the distal end of the flexible body 52, so that the stretching balloon 76 can axially stretch (and slightly straighten) the stretchable portion of the flexible body 52 adjacent to the stretching balloon 76. In a third step, the first locking balloon 74 is inflated again; and in a fourth step the second locking balloon 78 is deflated, with also the stretching balloon 76 being deflated, so that, while the tip of the flexible body 52 is locked by action of the inflated first locking balloon 74, the proximal part of the flexible body 52, including the second locking balloon 78, may be moved axially towards the tip with the first locking balloon 74 due to elastic contraction of the stretching balloon 76 and the adjacent portion of the flexible body 52 upon deflation of the stretching balloon 76.

By repeating such sequence of steps in a cyclic manner, the electrode array 50 may be moved axially into the cochlea. On the other hand, the electrode array 50 may be moved axially out of the cochlea, i.e. in the opposite direction, by interchanging the roll of the first and second locking balloons 74, 78 in the above sequence.

Figure 7:
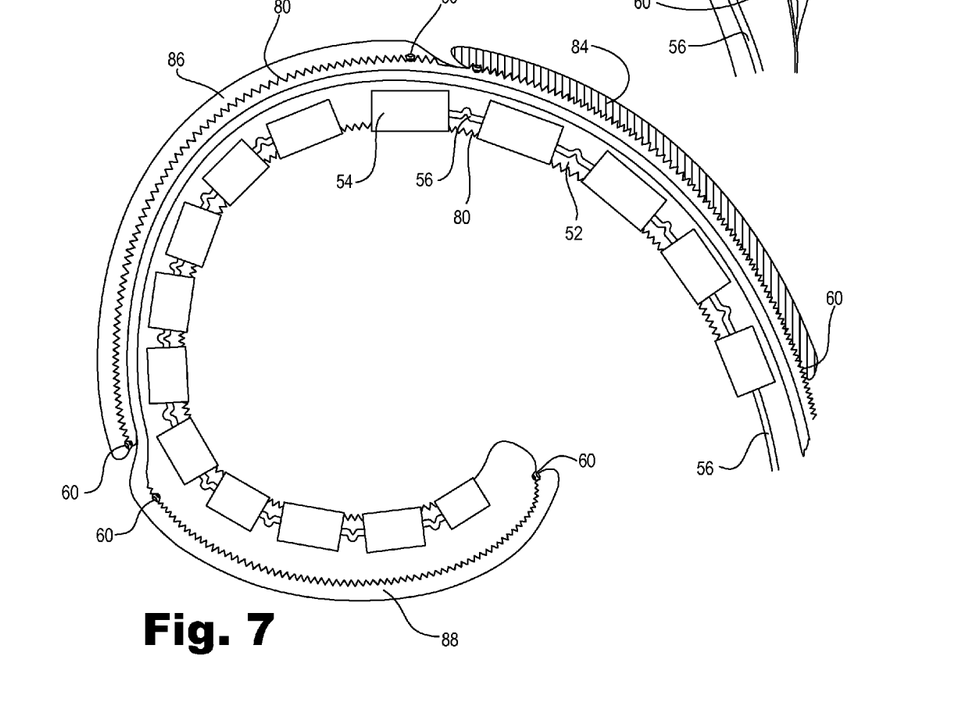
FIG. 7 is a view like FIG. 3A, wherein a still further alternative example is shown.

Another example of an electrode array 50 is shown in FIG. 7, wherein a plurality of separately inflatable/deflatable stretching balloons 84, 86 and 88 are provided at the side of the flexible body 52 facing away from the modiolus when the electrode array 50 is inserted into the cochlea 150. The balloons 84 to 88, which arranged axially one after the other, are attached to the flexible body 52 via an attachment point 60 at each of the ends of the respective balloon. The balloon 88 is located at the most apical position, and the balloon 84 is located at the most basal position. The portion of the flexible body 52 adjacent to the balloons 84 to 88 is axially stretchable in a similar manner as in the example of FIG. 6. The balloons 84 to 88 are arranged axially in series along at least part of the length of the flexible body 52. Each stretching balloon 84, 86, 88 is adapted to axially stretch the portion of the flexible body 52 adjacent to the respective stretching balloon, when fully inflated, and to allow that adjacent portion of the flexible body 52 to reassume, due to elastic forces, its original shape, i.e. to shorten with regard to the stretched state, when deflated.

The stretching balloons 84 to 88 allows a change in the length of the electrode array 50 to some extent in order to allow the electrode array 50 to more accurately adjust to the individual length of the patient's cochlea, while maintaining a medial contact location.

Moreover, such lengthening of the electrode array 50, as provided by such multiple stretching balloons 84 to 88, is particularly useful in a hybrid system applying not only electrical stimulation via the electrode contacts 54 but in addition acoustic stimulation (at the same ear or at the other ear) for making use of residual hearing. As such residual hearing was lost, the electrode array could be lengthened to allow stimulation to take over from the lost residual hearing, moving the most apical electrode contacts 54 further into the cochlea. Where the electrode array 50 could be adjusted while the recipient was awake, a stimulation could be provided to seek out octave intervals, for example, so as to adjust the electrode array not only mechanically but also optimally to the neural population of an individual recipient. Such approach could also be seen as an "air drill" where some moderate obstruction in the cochlea was not accessible to drill through, could be pushed through using a straightening balloon.

Figure 8:
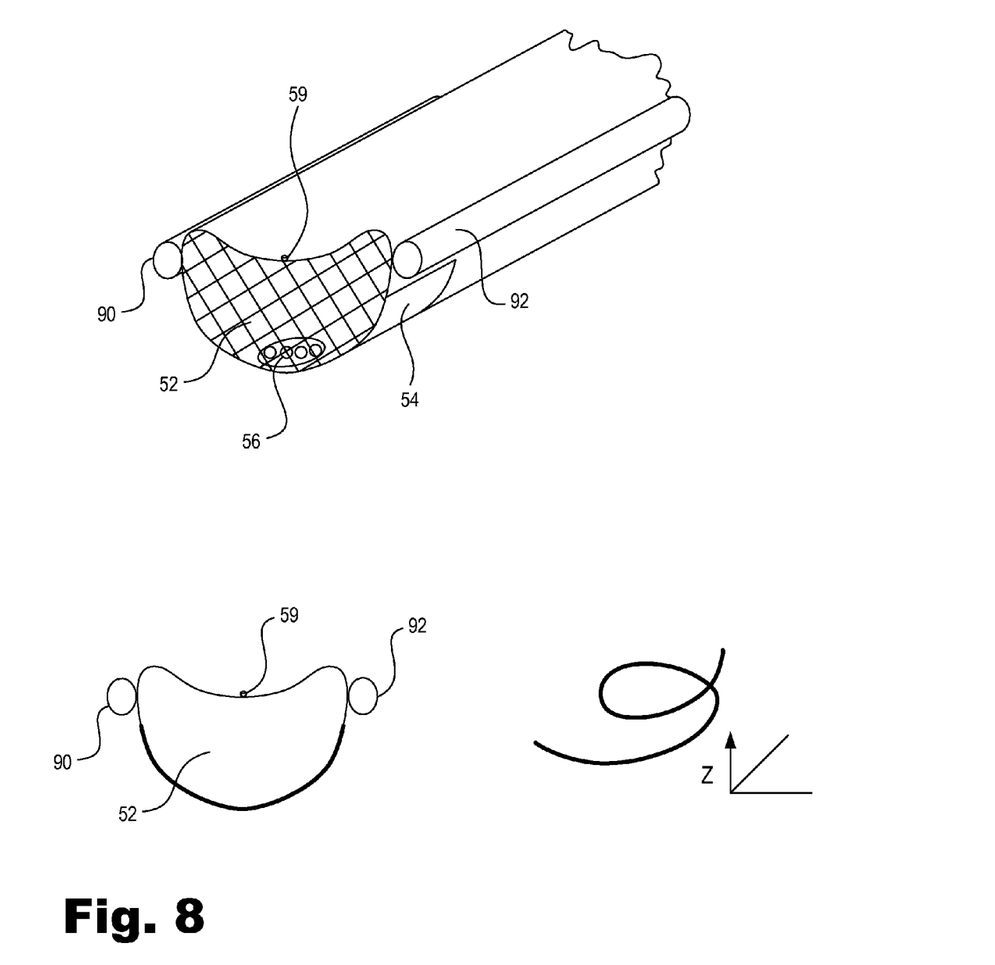
FIG. 8 is a perspective, partially cross-sectional, view of another example of an electrode array.

In FIG. 8 an example of an electrode array 50 is shown which is provided with two lateral balloons 90, 92 which are located at each of two opposite sides of the flexible body 52 and which extend axially along at least part of the length of the flexible body 52 (in FIG. 8 the axially extending inflatable balloon 58 provided for straightening the electrode array prior to insertion to the cochlea has been omitted, but the depression 59 provided for receiving such straightening balloon can be seen). The lateral balloons 90, 92 are arranged laterally with regard to the depression 59 and the respective straightening balloon 58.

The lateral balloons 90, 92 are adapted to change, upon inflation or deflation, a curvature of the flexible body 52 in a plane perpendicular to the plane of the pre-curved spiral shape in order to selectively change a helical extension of the flexible body by appropriate inflation or deflation of the lateral balloons 90, 92; in other words, the balloons 90, 92 thereby may act as "z-steering" balloons. Thereby, an articulated design can be implemented, making the rotational orientation of each contact 54 independent in order to account for helical twisting, so that placement of contacts 54 could be adjusted following implantation.

The idea here is to just help the electrode array deform in the right z direction so that it will better take up a helical-spiral shape without such pressure being imposed by the cochlear walls. Right and left cochlea will have the helical offset happen in different directions so these side balloons simply help adapt the array to go into either a right or left cochlea better. If multiple balloons were available on the sides a finer control could be achieved essentially keeping the array in the middle of the scala all the way through its insertion.

According to one example, the electrode array 50 may comprise sensors (indicated at 94 in FIG. 3A) for detecting a lateral wall pressure (i.e. the pressure resulting from the force by which the electrode array is laterally pressed against the cochlea wall) for use in a feedback control system (not shown) in order to minimize the force applied to the electrode array upon insertion into the cochlea.

Appropriate techniques, such as electric field imaging, could be used to detect contact of the electrode array with the medial wall of the cochlea in order to control deflation of the straightening balloon(s) 58, 58A-58D, during insertion of the electrode array into the cochlea; in particular, it may be used to stop deflation at the right time.

Also, fluoroscopy may be applied during insertion of the electrode array to verify that optimal automatic placement is achieved.

In particular, in case of multiple straightening balloons 58A to 58D, preoperative MRI or CT images of the cochlea may be obtained and used to plan the individual balloon diameters (i.e. the amount of gas/liquid by which the respective balloon is to be filled at a certain point in time) in order to enable semi-automatic implantation or explantation of the electrode array.

According to one embodiment, the content of the balloon(s) may be replaced or altered, after implantation, to form a gel in order to "freeze" the desired position to avoid long-term change through pressure loss. Ideally, such gel state could return to gas or fluid form (by transformation or replacement) in order to facilitate an atraumatic removal of the electrode array. This would require connecting a source of either gas or liquid to the balloon(s) and provoking a chemical reaction that restored the liquid nature of the balloons contents, possibly through partly or completely changing the content, a sort of dialysis of the balloon content.

The rotational orientation of the electrode contacts may be controllable through detection of individual impedances from each separate electrode contact.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear electrode array adapted for insertion into a human cochlea, comprising:
   a flexible body having a pre-curved spiral shape so as to conform with the curvature of a human cochlea;
   a plurality of stimulation electrode contacts spaced apart along a first side of the flexible body;
   a bundle of wires embedded within the flexible body for electrically connecting the electrode contacts to at least one stimulation signal source;
   at least one inflatable portion extending along at least part of a length of the flexible body, the at least one inflatable portion being adapted to straighten the flexible body, starting from the pre-curved shape, prior to insertion into the cochlea upon being inflated by being filled with gas or liquid, and to allow the flexible body to gradually reassume its pre-curved shape during insertion of the flexible body into the cochlea upon gradual withdrawal of gas or liquid from the at least one inflatable portion;
   wherein the at least one inflatable portion comprises at least one inflatable balloon attached to the flexible body only at attachment points at each of the ends of the at least one inflatable balloon.

2. The electrode array of claim 1, wherein the at least one inflatable balloon comprises a plurality of balloons which are inflatable separately from each other and which arranged in series along at least part of the length of the flexible body.

3. The electrode array of claim 2, wherein each of the plurality of balloons is connected to a dedicated supply tube, the supply tubes extending along the surface of the flexible body.

4. The electrode array of claim 1, wherein the at least one inflatable balloon has a tubular shape when fully inflated.

5. The electrode array of claim 4, wherein the at least one inflatable balloon has a substantially circular cross-section when fully inflated.

6. The electrode array of claim 1, wherein the at least one inflatable balloon is arranged at the side of the flexible body having the larger radius of curvature when the flexible body has its pre-curved shape, which is the side facing away from the modiolar wall of the cochlea.

7. The electrode array of claim 1, wherein the at least one inflatable portion is arranged at least in part within an axially extending depression of the flexible body.

8. The electrode array of claim 1, wherein the flexible body is provided laterally at each of two opposite sides at least one separately inflatable z-steering balloon adapted to change, upon inflation or deflation, a curvature of the flexible body in a plane perpendicular to the plane of the pre-curved spiral shape in order to selectively change the helical travel of the flexible body by inflation or deflation of the z-steering balloons.

9. The electrode array of claim 1, wherein the electrode array comprises sensors for detecting a pressure of a lateral cochlear wall, the wall opposite to the medial wall, or of the basilar membrane for use in a feedback control system that minimizes the force applied by the electrode array upon insertion into the cochlea.

10. A cochlear electrode array adapted for insertion into a human cochlea, comprising:
- a flexible body having a pre-curved spiral shape so as to conform with the curvature of a human cochlea;
- a plurality of stimulation electrode contacts spaced apart along a first side of the flexible body;
- a bundle of wires embedded within the flexible body for electrically connecting the electrode contacts to at least one stimulation signal source;
- at least one inflatable portion extending along at least part of a length of the flexible body, the at least one inflatable portion being adapted to straighten the flexible body, starting from the pre-curved shape, prior to insertion into the cochlea upon being inflated by being filled with gas or liquid, and to allow the flexible body to gradually reassume its pre-curved shape during insertion of the flexible body into the cochlea upon gradual withdrawal of gas or liquid from the at least one inflatable portion;
- wherein the at least one inflatable portion comprises at least one stretching balloon being adapted to straighten and axially stretch a portion of the flexible body located at the at least one stretching balloon when fully inflated and to allow said portion of the flexible body to reassume its pre-curved shape when deflated, with said portion of the flexible body being flexible in the axial direction for being axially stretched upon inflation of the at least one stretching balloon.

11. The electrode array of claim 10, wherein said portion of the flexible body is provided with wrinkled walls.

12. The electrode array of claim 10, wherein the at least one stretching balloon comprises a plurality of stretching balloons which are inflatable separately from each other and which arranged in series along at least part of the length of the flexible body.

* * * * *